(12) United States Patent
Urick

(10) Patent No.: US 6,203,485 B1
(45) Date of Patent: Mar. 20, 2001

(54) LOW ATTENUATION GUIDE WIRE FOR INTRAVASCULAR RADIATION DELIVERY

(75) Inventor: Michael J. Urick, Rogers, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/414,404

(22) Filed: Oct. 7, 1999

(51) Int. Cl.$^7$ ............................................. A61N 5/00
(52) U.S. Cl. ................................................ 600/3; 600/585
(58) Field of Search ................................. 600/1–8, 585

(56) References Cited

U.S. PATENT DOCUMENTS

| | | | |
|---|---|---|---|
| 2,546,761 | 3/1951 | Loftus | 128/1.2 |
| 2,862,108 | 11/1958 | Meilink | 250/106 |
| 2,955,208 | 10/1960 | Stevens | 250/108 |
| 3,060,924 | 10/1962 | Rush | 128/1.2 |
| 3,147,383 | 9/1964 | Prest | 250/108 |
| 3,324,847 | 6/1967 | Zoumboulis | 128/1.2 |
| 3,505,991 | 4/1970 | Hellerstein et al. | 128/1.1 |
| 3,643,096 | 2/1972 | Jeffries, Jr. et al. | 250/108 R |
| 3,669,093 | 6/1972 | Sauerwein et al. | 128/1.1 |
| 3,674,006 | 7/1972 | Holmer | 128/1.2 |
| 3,750,653 | 8/1973 | Simon | 128/1.2 |

(List continued on next page.)

FOREIGN PATENT DOCUMENTS

| | | |
|---|---|---|
| 2166915 | 8/1996 | (CA). |
| 91 02 312 | 8/1992 | (DE). |
| 195 26 680 A1 | 1/1997 | (DE). |
| 197 54 870 A1 | 8/1998 | (DE). |
| 197 24 233 C1 | 12/1998 | (DE). |
| 197 58 234 | 7/1999 | (DE). |
| 198 07 727 | 7/1999 | (DE). |
| 198 25 563 | 12/1999 | (DE). |
| 198 25 999 | 12/1999 | (DE). |
| 198 26 000 | 12/1999 | (DE). |

(List continued on next page.)

OTHER PUBLICATIONS

Tjho–Heslinga et al., "Results of ruthenium irradiation of uveal melanona", *Radiotherapy On cology*, vol. 29, pp 33–38, 1993.

Lommatzsch et al., "Radiation effects on the optic nerve observed after brachytherapy of choroidal melanomas with 106Ru/106Rh plaques", *Graefe's Arch. Clin. Exp. Ophthalmology* vol. 232, pp. 482–487, 1994.

*Radiotherapy of Intraoculare and Orbital Tumors*, Springer–Verlak publisher, Berlin Heidelberg and New York, copyright 1993, pp. 23–30 and 363–367.

Fackelmann, "Harbinger of a Heart Attack", *Science News*, vol. 151, Jun. 14, 1997, pp. 374–75.

Raloff, "Nuclear Medicine Gets Friendlier—Experimental Therapies Seek to Poison Just the Disease", *Science News*, vol. 152, Jul. 19, 1997, pp. 40–41.

Sutherland, "Managing Cancer Through Synergy", *Administrative Radiology Journal*, Nov. 1996, pp. 21–27.

*Primary Examiner*—Samuel G. Gilbert
*Assistant Examiner*—Joseph A. Cadugan
(74) *Attorney, Agent, or Firm*—Crompton, Seager & Tufte, LLC

(57) ABSTRACT

A low attenuation guide wire for use in combination with a radiation device for intravascular ionizing radiation therapy. The distal region of the guide wire is less attenuating to ionizing radiation than the proximal region and may be disposed adjacent the radiation emitting portion of the radiation device without significantly compromising the emission of radiation. Thus, the guide wire does not need to be removed or retracted in order to effectively deliver ionizing radiation to the vascular target site.

46 Claims, 3 Drawing Sheets

U.S. PATENT DOCUMENTS

| | | | |
|---|---|---|---|
| 3,811,426 | 5/1974 | Culver et al. | 128/1.2 |
| 3,861,380 | 1/1975 | Chassagne et al. | 128/1.2 |
| 3,866,050 | 2/1975 | Whitfield | 250/497 |
| 3,927,325 | 12/1975 | Hungate et al. | 250/435 |
| 4,096,862 | 6/1978 | DeLuca | 128/348 |
| 4,220,864 | 9/1980 | Saurwein et al. | 250/497 |
| 4,225,790 | 9/1980 | Parsons, Jr. et al. | 250/497 |
| 4,244,357 | 1/1981 | Morrison | 128/1.2 |
| 4,281,252 | 7/1981 | Parsons, Jr. et al. | 250/497 |
| 4,314,157 | 2/1982 | Gaines | 250/497 |
| 4,364,376 | 12/1982 | Bigham | 128/1.1 |
| 4,584,991 | 4/1986 | Tokita et al. | 128/1.1 |
| 4,588,395 | 5/1986 | Lemelson | 604/59 |
| 4,631,415 | 12/1986 | Sauerwein et al. | 250/497.1 |
| 4,702,228 | 10/1987 | Russell, Jr. et al. | 128/1.2 |
| 4,706,652 | 11/1987 | Horowitz | 128/1.2 |
| 4,763,642 | 8/1988 | Horowitz | 128/1.2 |
| 4,763,671 | 8/1988 | Goffinet | 128/786 |
| 4,782,834 | 11/1988 | Maguire et al. | 128/344 |
| 4,784,116 | 11/1988 | Russell, Jr. et al. | 128/1.2 |
| 4,815,449 | 3/1989 | Horowitz | 600/7 |
| 4,819,618 | 4/1989 | Liprie | 600/7 |
| 4,851,694 | 7/1989 | Rague et al. | 250/497.1 |
| 4,861,520 | 8/1989 | van't Hooft et al. | 252/644 |
| 4,881,937 | 11/1989 | van't Hooft et al. | 600/3 |
| 4,897,076 | 1/1990 | Puthawala et al. | 600/7 |
| 4,936,823 | 6/1990 | Colvin et al. | 600/7 |
| 4,963,128 | 10/1990 | Daniel et al. | 600/7 |
| 4,969,863 | 11/1990 | van't Hooft et al. | 600/3 |
| 4,976,266 | 12/1990 | Huffman et al. | 128/659 |
| 4,976,680 | 12/1990 | Hayman et al. | 600/7 |
| 4,976,690 | 12/1990 | Solar et al. | 604/96 |
| 5,030,194 | 7/1991 | Van't Hooft | 600/3 |
| 5,032,113 | 7/1991 | Burns | 604/6 |
| 5,059,166 | 10/1991 | Fischell et al. | 600/3 |
| 5,084,001 | 1/1992 | Van't Hooft et al. | 600/3 |
| 5,084,002 | 1/1992 | Liprie | 600/7 |
| 5,092,834 | 3/1992 | Bradshaw et al. | 600/7 |
| 5,103,395 | 4/1992 | Spako et al. | 364/413.26 |
| 5,106,360 | 4/1992 | Ishiwara et al. | 600/2 |
| 5,120,973 | 6/1992 | Rohe et al. | 250/497.1 |
| 5,139,473 | 8/1992 | Bradshaw et al. | 600/3 |
| 5,141,487 | 8/1992 | Liprie | 600/7 |
| 5,147,282 | 9/1992 | Kan | 600/1 |
| 5,163,896 | 11/1992 | Suthanthiran et al. | 600/8 |
| 5,176,617 | 1/1993 | Fischell et al. | 600/3 |
| 5,183,455 | 2/1993 | Hayman et al. | 600/7 |
| 5,199,939 | 4/1993 | Dake et al. | 600/3 |
| 5,213,561 | 5/1993 | Weinstein et al. | 600/7 |
| 5,261,879 | 11/1993 | Brill | 604/96 |
| 5,267,960 | 12/1993 | Hayman et al. | 604/106 |
| 5,282,781 | 2/1994 | Liprie | 600/3 |
| 5,302,168 | 4/1994 | Hess | 600/3 |
| 5,344,383 | 9/1994 | Liping | 600/3 |
| 5,354,257 | 10/1994 | Roubin et al. | 600/7 |
| 5,370,685 | 12/1994 | Stevens | 623/2 |
| 5,391,139 | 2/1995 | Edmundson | 600/7 |
| 5,395,300 | 3/1995 | Liprie | 600/3 |
| 5,405,309 | 4/1995 | Carden, Jr. | 600/3 |
| 5,409,015 | 4/1995 | Palermo | 128/772 |
| 5,411,466 | 5/1995 | Hess | 600/3 |
| 5,425,720 | 6/1995 | Rogalsky et al. | 604/198 |
| 5,429,582 | 7/1995 | Williams | 600/2 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,503,614 | 4/1996 | Liprie | 600/7 |
| 5,532,122 | 7/1996 | Drukier | 435/5 |
| 5,538,494 | 7/1996 | Matsuda | 600/1 |
| 5,540,659 | 7/1996 | Teirstein | 604/104 |
| 5,556,389 | 9/1996 | Liprie | 604/264 |
| 5,575,749 | 11/1996 | Liprie | 600/3 |
| 5,575,771 | 11/1996 | Walinsky | 604/96 |
| 5,605,530 | 2/1997 | Fischell et al. | 600/3 |
| 5,611,767 | 3/1997 | Williams | 600/2 |
| 5,616,114 | 4/1997 | Thornton et al. | 600/3 |
| 5,618,266 | 4/1997 | Liprie | 604/21 |
| 5,624,372 | 4/1997 | Liprie | 600/3 |
| 5,643,171 | 7/1997 | Bradshaw et al. | 600/1 |
| 5,649,924 | 7/1997 | Everett et al. | 606/15 |
| 5,653,683 | 8/1997 | D'Andrea | 604/21 |
| 5,662,580 | 9/1997 | Bradshaw et al. | 600/3 |
| 5,674,177 | 10/1997 | Hehrlein et al. | 600/3 |
| 5,683,345 | 11/1997 | Waksman et al. | 600/3 |
| 5,688,220 | 11/1997 | Verin et al. | 600/1 |
| 5,707,332 | 1/1998 | Weinberger | 600/3 |
| 5,713,828 | 2/1998 | Coniglione | 600/7 |
| 5,720,717 | 2/1998 | D'Andrea | 604/21 |
| 5,722,984 | 3/1998 | Fischell et al. | 606/198 |
| 5,728,042 | 3/1998 | Schwager | 600/3 |
| 5,730,698 | 3/1998 | Fischell et al. | 600/3 |
| 5,776,099 | 7/1998 | Tremulis | 604/96 |
| 5,782,740 | 7/1998 | Schneiderman | 600/1 |
| 5,782,742 | 7/1998 | Crocker et al. | 600/3 |
| 5,795,286 | 8/1998 | Fischell et al. | 600/3 |
| 5,800,333 | 9/1998 | Liprie | 600/3 |
| 5,803,895 | 9/1998 | Kronholz et al. | 600/3 |
| 5,807,231 | 9/1998 | Liprie | 600/3 |
| 5,816,259 | 10/1998 | Rose | 128/898 |
| 5,816,999 | 10/1998 | Bischoff et al. | 600/3 |
| 5,820,553 | 10/1998 | Hughes | 600/426 |
| 5,822,291 | 3/1999 | Bradshaw et al. | 600/3 |
| 5,833,593 | 11/1998 | Liprie | 600/3 |
| 5,840,008 | 11/1998 | Klein et al. | 600/3 |
| 5,840,009 | 11/1998 | Fischell et al. | 600/3 |
| 5,840,064 | 11/1998 | Liprie | 604/96 |
| 5,843,163 | 12/1998 | Wall | 623/1 |
| 5,851,171 | 12/1998 | Gasson | 600/3 |
| 5,851,172 | 12/1998 | Bueche et al. | 600/7 |
| 5,855,546 * | 1/1999 | Hastings et al. | 600/3 |
| 5,857,956 | 1/1999 | Liprie | 600/7 |
| 5,863,284 | 1/1999 | Klein | 600/3 |
| 5,863,285 | 1/1999 | Coletti | 600/3 |
| 5,865,720 | 2/1999 | Hastings et al. | 600/3 |
| 5,871,436 | 2/1999 | Eury | 600/3 |
| 5,871,437 | 2/1999 | Alt | 600/3 |
| 5,873,811 | 2/1999 | Wang et al. | 600/5 |
| 5,879,282 | 3/1999 | Fischell et al. | 600/3 |
| 5,882,290 | 3/1999 | Kume | 600/3 |
| 5,882,291 * | 3/1999 | Bradshaw et al. | 600/3 |
| 5,891,091 | 4/1999 | Teirstein | 604/104 |
| 5,897,573 | 4/1999 | Rosenthal et al. | 606/224 |
| 5,899,882 | 5/1999 | Waksman et al. | 604/96 |
| 5,906,573 | 5/1999 | Aretz | 600/3 |
| 5,910,101 | 6/1999 | Andrews et al. | 600/3 |
| 5,910,102 | 6/1999 | Hastings | 600/3 |
| 5,913,813 | 6/1999 | Williams et al. | 600/3 |
| 5,916,143 | 6/1999 | Apple et al. | 600/3 |
| 5,919,126 | 7/1999 | Armini | 600/3 |
| 5,924,973 | 7/1999 | Weinberger | 600/3 |
| 5,924,974 | 7/1999 | Loffler | 600/3 |
| 5,938,582 | 8/1999 | Ciamacco, Jr. et al. | 600/3 |
| 5,947,889 | 9/1999 | Hehrlein | 600/3 |
| 5,947,924 | 9/1999 | Liprie | 604/96 |
| 5,947,958 | 9/1999 | Woodard et al. | 606/1.5 |
| 5,957,829 | 9/1999 | Thornton | 600/3 |
| 5,961,439 | 10/1999 | Chernomorsky et al. | 600/4 |
| 5,967,966 | 10/1999 | Kronholz et al. | 600/3 |
| 5,971,909 | 10/1999 | Bradshaw et al. | 600/3 |
| 5,976,106 | 11/1999 | Verin et al. | 604/96 |
| 5,997,462 | 12/1999 | Loffler | 600/3 |

| | | | |
|---|---|---|---|
| 5,997,463 | 12/1999 | Cutrer | 600/8 |
| 6,010,445 | 1/2000 | Armini et al. | 600/3 |
| 6,013,019 | 1/2000 | Fischell et al. | 600/3 |
| 6,013,020 | 1/2000 | Meloul et al. | 600/7 |
| 6,024,690 | 2/2000 | Lee et al. | 600/3 |
| 6,030,333 | 2/2000 | Sioshansi et al. | 600/3 |
| 6,033,357 * | 3/2000 | Ciezki et al. | 600/3 |
| 6,074,339 * | 6/2000 | Gambale et al. | 600/3 |

FOREIGN PATENT DOCUMENTS

| | | |
|---|---|---|
| 198 29 447 | 1/2000 | (DE) . |
| 0 360 582 | 8/1990 | (EP) . |
| 0 514 913 A2 | 11/1992 | (EP) . |
| 0 633 041 A1 | 1/1995 | (EP) . |
| 0 686 342 A1 | 12/1995 | (EP) . |
| 0 688 580 A1 | 12/1995 | (EP) . |
| 0 696 906 B1 | 2/1996 | (EP) . |
| 0 749 764 A1 | 12/1996 | (EP) . |
| 0 754 472 A2 | 1/1997 | (EP) . |
| 0 754 473 A2 | 1/1997 | (EP) . |
| 0 593 136 B1 | 3/1997 | (EP) . |
| 0 778 051 A1 | 6/1997 | (EP) . |
| 0 801 961 A2 | 10/1997 | (EP) . |
| 0 810 004 | 12/1997 | (EP) . |
| 0 813 894 A2 | 12/1997 | (EP) . |
| 0 629 380 B1 | 7/1998 | (EP) . |
| 0 865 803 | 9/1998 | (EP) . |
| 0 904 799 | 3/1999 | (EP) . |
| 10071210 | 3/1998 | (JP) . |
| WO 86/03124 | 6/1986 | (WO) . |
| WO 93/04735 | 3/1993 | (WO) . |
| WO 94/25106 | 11/1994 | (WO) . |
| WO 94/26205 | 11/1994 | (WO) . |
| WO 95/07732 | 3/1995 | (WO) . |
| WO 96/06654 | 3/1996 | (WO) . |
| WO 96/10436 | 4/1996 | (WO) . |
| WO 96/13303 | 5/1996 | (WO) . |
| WO 96/14898 | 5/1996 | (WO) . |
| WO 96/17654 | 6/1996 | (WO) . |
| WO 96/22121 | 7/1996 | (WO) . |
| WO 96/29943 | 10/1996 | (WO) . |
| WO 96/40352 | 12/1996 | (WO) . |
| WO 97/07740 | 3/1997 | (WO) . |
| WO 97/09937 | 3/1997 | (WO) . |
| WO 97/17029 | 5/1997 | (WO) . |
| WO 97/18012 | 5/1997 | (WO) . |
| WO 97/19706 | 6/1997 | (WO) . |
| WO 97/25102 | 7/1997 | (WO) . |
| WO 97/25103 | 7/1997 | (WO) . |
| WO 97/40889 | 11/1997 | (WO) . |
| WO 98/01183 | 1/1998 | (WO) . |
| WO 98/01184 | 1/1998 | (WO) . |
| WO 98/01185 | 1/1998 | (WO) . |
| WO 98/01186 | 1/1998 | (WO) . |
| WO 98/11936 | 3/1998 | (WO) . |
| WO 98/16151 | 4/1998 | (WO) . |
| WO 98/20935 | 5/1998 | (WO) . |
| WO 98/25674 | 6/1998 | (WO) . |
| WO 98/29049 | 7/1998 | (WO) . |
| WO 98/30273 | 7/1998 | (WO) . |
| WO 98/34681 | 8/1998 | (WO) . |
| WO 98/36788 | 8/1998 | (WO) . |
| WO 98/36790 | 8/1998 | (WO) . |
| WO 98/36796 | 8/1998 | (WO) . |
| WO 98/39052 | 9/1998 | (WO) . |
| WO 98/39062 | 9/1998 | (WO) . |
| WO 98/39063 | 9/1998 | (WO) . |
| WO 98/40032 | 9/1998 | (WO) . |
| WO 98/46309 | 10/1998 | (WO) . |
| WO 98/55179 | 12/1998 | (WO) . |
| WO 98/57706 | 12/1998 | (WO) . |
| WO 99/01179 | 1/1999 | (WO) . |
| WO 99/02219 | 1/1999 | (WO) . |
| WO 99/04706 | 2/1999 | (WO) . |
| WO 99/04856 | 2/1999 | (WO) . |
| WO 99/10045 | 3/1999 | (WO) . |
| WO 99/21615 | 5/1999 | (WO) . |
| WO 99/21616 | 5/1999 | (WO) . |
| WO 99/22774 | 5/1999 | (WO) . |
| WO 99/22775 | 5/1999 | (WO) . |
| WO 99/22812 | 5/1999 | (WO) . |
| WO 99/22815 | 5/1999 | (WO) . |
| WO 99/24116 | 5/1999 | (WO) . |
| WO 99/24117 | 5/1999 | (WO) . |
| WO 99/29354 | 6/1999 | (WO) . |
| WO 99/29370 | 6/1999 | (WO) . |
| WO 99/29371 | 6/1999 | (WO) . |
| WO 99/30779 | 6/1999 | (WO) . |
| WO 99/34969 | 7/1999 | (WO) . |
| WO 99/36121 | 7/1999 | (WO) . |
| WO 99/39628 | 8/1999 | (WO) . |
| WO 99/40962 | 8/1999 | (WO) . |
| WO 99/40970 | 8/1999 | (WO) . |
| WO 99/40972 | 8/1999 | (WO) . |
| WO 99/40973 | 8/1999 | (WO) . |
| WO 99/40974 | 8/1999 | (WO) . |
| WO 99/42162 | 8/1999 | (WO) . |
| WO 99/42163 | 8/1999 | (WO) . |
| WO 99/42177 | 8/1999 | (WO) . |
| WO/40971 | 8/1999 | (WO) . |
| WO 99/44686 | 9/1999 | (WO) . |
| WO 99/44687 | 9/1999 | (WO) . |
| WO 99/49935 | 10/1999 | (WO) . |
| WO 99/56825 | 11/1999 | (WO) . |
| WO 99/56828 | 11/1999 | (WO) . |
| WO 99/61107 | 12/1999 | (WO) . |
| WO 99/62598 | 12/1999 | (WO) . |
| WO 99/66979 | 12/1999 | (WO) . |
| WO 00/03292 | 1/2000 | (WO) . |
| WO 00/04838 | 2/2000 | (WO) . |
| WO 00/04953 | 2/2000 | (WO) . |
| WO 00/09212 | 2/2000 | (WO) . |

* cited by examiner

LOW ATTENUATION GUIDE WIRE FOR INTRAVASCULAR RADIATION DELIVERY

FIELD OF THE INVENTION

The present invention generally relates to devices and methods for intravascular ionizing radiation therapy. More specifically, the present invention relates to improved guide wires for intravascular ionizing radiation therapy.

BACKGROUND OF THE INVENTION

Intravascular ionizing radiation therapy is being used increasingly to treat vascular disease, and has been proposed as both a primary and a secondary therapy for treating vascular restrictions. Clinical studies have shown that ionizing radiation may be effectively used to inhibit or prevent restenosis after percutaneous translumenal coronary angioplasty (PCTA). For example, U.S. Pat. No. 5,643,171 to Bradshaw et al disclose a method and apparatus for intravascular radiotherapy for prevention of restenosis following angioplasty or other procedures that cause smooth cell proliferation.

As best seen in FIG. 1 of Bradshaw et al., a catheter 10 is illustrated having an elongate shaft 12 with a distal treatment section 14 and a distal tip 16. Attached to the distal treatment section 14 is a centering balloon 40. The elongate shaft 12 also includes a treatment channel 20 as best seen in FIG. 2. The treatment channel 20 allows for the introduction of a source wire (not shown) having a distal radioactive section. With this design, the catheter 10 allegedly maintains the treatment channel 20, and thus the source wire, in the center of the vessel, despite vessel curvature in the region the vessel being treated, for uniform delivery of radiation.

One disadvantage of this particular design is the arrangement of the catheter 10 relative to the guide wire 32, which may block radiation from reaching the vessel wall 30. In particular, the shaft 12 includes a distal Monorail®-type guide wire lumen 24 that allows the catheter to be advanced over the guide wire 32 until the treatment section 14 is disposed in the target area 34 of the blood vessel 30. The distal Monorail®-type lumen 24 opens at the distal tip of the shaft and exits through the lateral surface of the shaft 12 distal of the balloon 40. Thus, the guide wire 32 extends adjacent the catheter 10 and centering balloon 40 at the target area 34 of the blood vessel 30.

Because guide wires are conventionally formed of metal alloys such as stainless steel, the guide wire 32 will tend to attenuate radiation emitted by the source wire disposed in the treatment channel 20. Attenuation of the radiation causes a shadow to be cast on the vessel wall 30 in the target area 34 such that a portion of the target area 34 is not uniformly exposed to ionizing radiation. Failure to expose the entire target area 34 to ionizing radiation may give rise to restenosis at the unexposed or underexposed region. The recurrence of restenosis anywhere in the target area 34 is clearly disadvantageous since the primary objective of the therapy is to prevent or otherwise inhibit restenosis.

The initial response to solving this problem may be to move (e.g., retract or withdraw) the guide wire 32 to avoid blocking radiation. However, retraction of guide wire in the proximal direction such that the guide wire 32 does not extend across the target area 34, is not a particularly viable option because vascular access across the target area 34 would be lost and access to the guide wire lumen 24 at the distal tip of the shaft 12 would also be lost. In many instances, it is undesirable to lose vascular access across the target area 34 since the restriction may recoil rendering it difficult if not impossible to renavigate the guide wire 32 across the target site 34. Without the guide wire 32 disposed across the target area 34, it would be difficult to redilate or otherwise treat the vascular restriction. In addition, losing access to the guide wire lumen 24 makes it difficult, if not impossible, to steer or guide the catheter 10 through the vascular channel. Thus, it is extremely undesirable to retract the guide wire 32 in the proximal direction. Because it is undesirable to retract the guide wire 32 in the proximal direction, the guide wire 32 must be left in place where it will inevitably attenuate radiation emitted from the source wire.

SUMMARY OF THE INVENTION

The present invention overcomes these disadvantages by providing a low attenuation guide wire for use in combination with a radiation device (e.g., source wire) having a distal portion emitting ionizing radiation. The guide wire includes a proximal region and a distal region, wherein the distal region is less attenuating to ionizing radiation than the proximal region. The distal region of the guide wire may remain disposed adjacent the distal ionizing radiation emitting portion of the radiation device without significantly compromising the emission or absorption of radiation. Thus, the guide wire does not need to be removed or retracted in order to effectively deliver ionizing radiation to the vascular target site. This is particularly beneficial when it is desirable to maintain vascular access across the target site and when it is desirable to use rapid exchange type catheters (e.g., Monorail® catheters).

The distal region may be less attenuating to low energy gamma, high energy gamma, and/or beta radiation, depending on the material(s) selected and the attenuation characteristics desired. The material(s) selected may have a lower atomic number, a lower atomic weight, and/or a lower density than the proximal region, also depending the attenuation characteristics desired for different types of ionizing radiation. The region less attenuating to ionizing radiation may comprise one or more polymers, metals, or composites thereof. Preferably, the distal end of the distal region is relatively more radiopaque to facilitate radiographic visualization and fluoroscopic navigation.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
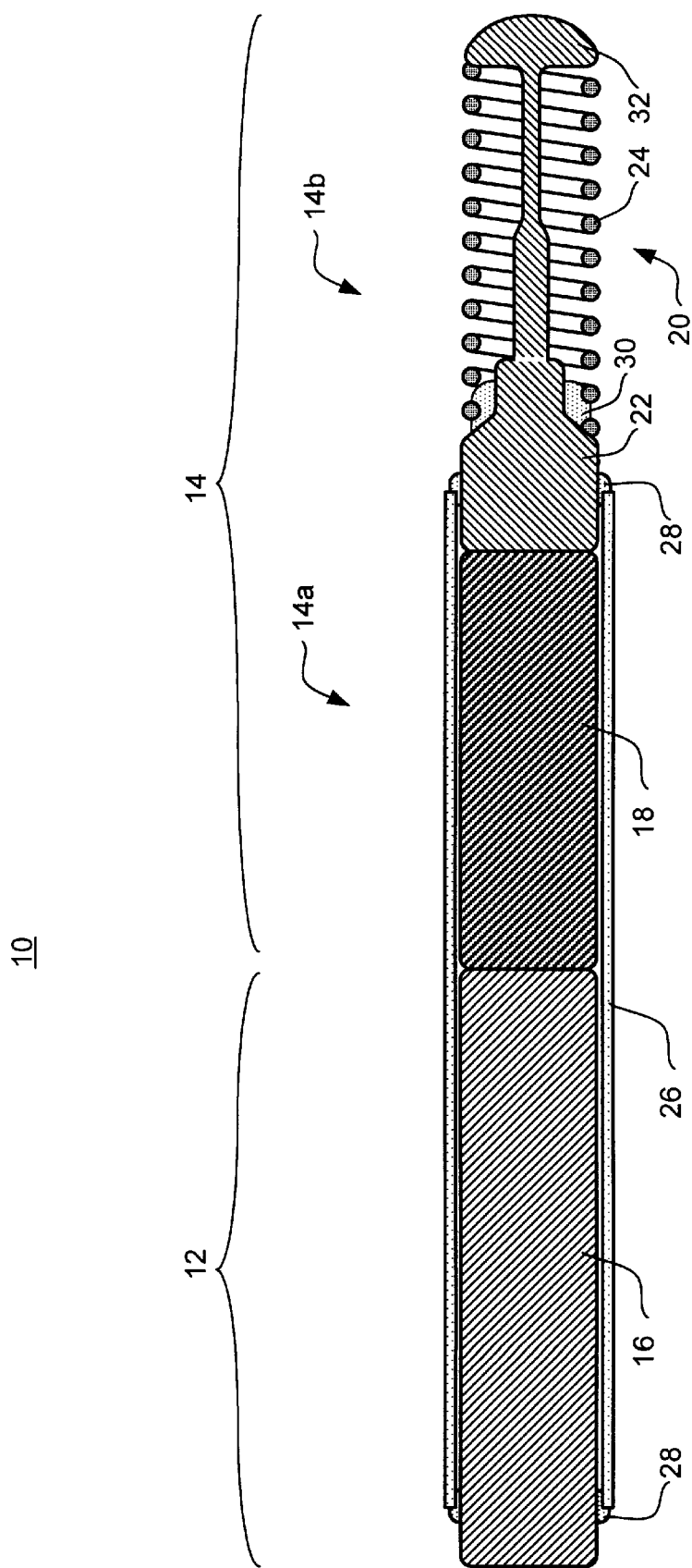
FIG. 1 is a longitudinal cross-sectional view of a first embodiment of a low attenuation guide wire of the present invention.

Refer now to FIG. 1 which illustrates a longitudinal cross-sectional view of a first embodiment of a low attenuation guide wire 10 of the present invention. Guide wire 10 is particularly useful in combination with a Monorail®-type radiation device having a distal portion emitting ionizing radiation. For example, guide wire 10 may be used in place of guide wire 44 as described in European Patent Application No. 688 580 A1 to Verin et al., or in place of guide wire 32 as described in U.S. Pat. No. 5,643,171 to Bradshaw et al., both of which are hereby incorporated by reference. Guide wire 10 is suitable for use in combination with wide variety of radiation devices wherein the radiation device is adapted to be advanced over a guide wire. Such radiation devices are well known in the art and have been described herein on a limited basis for purposes of simplicity and clarity. In addition, although particularly suitable for radiation devices, those skilled in the art will recognize that guide wire 10 is also suitable for use in combination with other non-radiation devices such as over-the-wire (OTW) balloon catheters, guide catheters, atherectomy catheters, etc.

Guide wire 10 includes an elongate shaft having a proximal region 12 and a distal region 14. The distal region 14 includes a proximal end portion 14a and a distal end portion 14b. Proximal end portion 14a of distal region 14 may also be referred to as a mid-portion 14a. The guide wire 10, including the proximal region 12 and the distal region 14 is sized to navigate the human vasculature from an access site to a remote target site. For example, guide wire 10 may have a diameter of approximately 0.010 to 0.022 inches depending on the inside diameter of the vasculature being navigated, and a length ranging from 60 to 350 centimeters depending on the distance from the access site to the target site. The guide wire 10 may be longer or be capable of attachment to an extension wire to provide the exchange length necessary for some OTW catheters.

Assuming a nominal length of approximately 150 centimeters, such as for coronary applications, the proximal region 12 may have a length of approximately 136–146 centimeters, the distal region 14 may have a length ranging from 6–40 centimeters. The proximal end portion 14a may have a length ranging from 34–38 centimeters and the distal end portion 14b may have a length ranging from 2–6 centimeters. Those skilled in the art will recognize that these dimensions are merely exemplary and may be modified depending on the desired performance characteristics of the guide wire 10 and the particular vascular anatomy being navigated.

The proximal region 12 of the guide wire 10 includes a core member 16, comprising a conventional guide wire material such as stainless steel, nitinol, or the like. The proximal end portion 14a of the distal region 14 includes a core member 18 comprising a material that is less attenuating (i.e., more transparent) to ionizing radiation the material of the core member 16 of the proximal region 12. The distal end portion 14b of the distal region 14 includes a spring tip 20 having a core member 22 and a coil member 24 which are more radiopaque than the material of the core member 18 of the proximal end portion 14a.

Core member 16 may be connected to core member 18 by a number of suitable means. For example, if core member 16 and core member 18 are formed of compatible materials, the distal end of core member 16 may be welded, soldered or brazed to the proximal end of core member 18. Similarly, if the material of core member 18 is compatible with the material of core member 22, the distal end of core member 18 may be welded, soldered or brazed to the proximal end of core member 22. Alternatively, the ends of core members 16, 18 and 22 may be connected using a suitable adhesive. To improve the integrity of the connections, a polymer jacket 26 may be disposed about the core members 16, 18 and 22. The polymer jacket 26 does not significantly increase attenuation of the proximal end portion 14a. The proximal end of the polymer jacket 26 may be connected to the proximal end of core member 16 utilizing a suitable adhesive 28. Similarly, the distal end of polymer jacket 26 may be connected to the proximal end of core member 22 utilizing adhesive 28.

Coil member 24 may be secured to core member 22 utilizing conventional means. For example, the proximal end of coil member 24 may be connected to the proximal end of core member 22 utilizing a solder or braze joint 30, assuming suitable and compatible materials are selected for coil member 24 and core member 22. The distal end of coil member 24 may be connected to the distal end of core member 22 by welding the materials together to form a atramatic weld ball 32.

As mentioned previously, the proximal end portion 14a of the distal region 14 is less attenuating (i.e., more transparent) to ionizing radiation than the proximal region 12. The material selected for the core member 18 in the region 14a less attenuating to ionizing radiation may be selected from the materials as identified in Group A of Table 1. These materials may be used in pure form or may be combined with other materials. For example, the material comprising the region 14a less attenuating to ionizing radiation may comprise a compound, an alloy, a composite, etc. An example of a composite is a polymer tube reinforced with carbon, aluminum, or glass fibers in the form of a coil, braid, or other suitable structure. Examples of polymers suitable for such a composite include polyethelene, polyurethane, polyiomid, polyamid, nylon, ect.,

TABLE 1

| Group | Material | Atomic No. | Atomic Wt. | Density (g/cm³) |
|---|---|---|---|---|
| A | Polymer | 6.5* | 13.01* | 0.9–1.2** |
|  | Graphite | 6 | 12.01 | 2.3 |
|  | Aluminum | 13 | 26.98 | 2.70 |
|  | Glass | 14 | 28.09 | 2.3 |
| B | Titanium | 22 | 47.88 | 4.5 |
|  | Nitinol | 25.3* | 53.29* | 6.7 |
|  | 304V SST | 25.9* | 54.50* | 7.9 |
| C | Tungsten | 74 | 183.84 | 19.3 |
|  | Platinum | 78 | 195.08 | 21.5 |

Notes:
*Estimated value
**Estimated range
Atomic weight based on carbon-12

The specific material or combination of materials selected from Group A is not critical as long as the region 14a is less attenuating to ionizing radiation. Generally speaking, the materials listed in Group A are less attenuating ionizing radiation due to the relatively low atomic weight and density. Note that if a pure material is used, the atomic weight and density values may be obtained from Table 1. If a combination of materials (e.g., compound, an alloy, a composite, etc.) are utilized, the atomic weight and density values may be estimated by taking into account the ratio of each material used, in addition to the cross-sectional geometry and area occupied by the respective materials.

With this in mind, the region 14a less attenuating to ionizing radiation may have an atomic number of less than 22, preferably less than 15, and more preferably less than 7. Similarly, the region less attenuating to ionizing radiation may have an atomic weight 15 of less than 47, preferably less than 29, and most preferably less than 13. Similarly, the region 14a less attenuating to ionizing radiation may have a density of less than 4.5 g/cm³, preferably less than 2.3 g/cm³, and more preferably less than 2.0 g/cm³.

Generally, low energy gamma radiation is most sensitive to the atomic weight of the selected material, high energy gamma radiation is most sensitive to the density of the selected material, and beta radiation is most sensitive to both the atomic weight and density of the selected material. With this in mind, the selection of material for region 14a may be based on the particular radioisotope to be used. If a low energy gamma ionizing radiation source is to be used, a low atomic weight material from Group A may be utilized for the proximal end portion 14a. If a high energy gamma ionizing radiation source is to be used, a low density material selected from Group A may be used. If a beta ionizing radiation source is to be used, a low atomic weight and low density material may be selected from Group A for the core member 18.

The core member 16 of the proximal region 12 and the core member 22 of the spring tip 20 may be formed of conventional materials such as those listed in Group B of Table 1. Similarly, the coil 24 of spring tip 20 may be formed of conventional materials such as those listed in Group C of Table 1. The materials identified in Group A are relatively less attenuating to ionizing radiation than the materials of Groups B and C. The materials identified in Group C are relatively more radiopaque than the materials of Groups A and B.

As can be appreciated from the data contained in Table 1, the material or materials used for the core member 18 of the proximal end portion 14a are less attenuating to ionizing radiation than the materials used for the distal end portion 14b and the proximal region 12, by virtue of the relatively lower atomic number, atomic weight and density. Thus, the lower atomic number, atomic weight and density of the materials listed in Group A of Table 1 render the proximal end portion 14a less attenuating to ionizing radiation than both the distal end portion 14b and the proximal region 12. If a low energy gamma ionizing radiation source is to be used, a low atomic weight from Group A may be utilized for the proximal end portion 14a. If a high energy gamma ionizing radiation source is to be used, a low density material selected from Group A may be used. If a beta ionizing radiation source is to be used, a low atomic weight and low density material may be selected from Group A for the core member 18.

Figure 2:
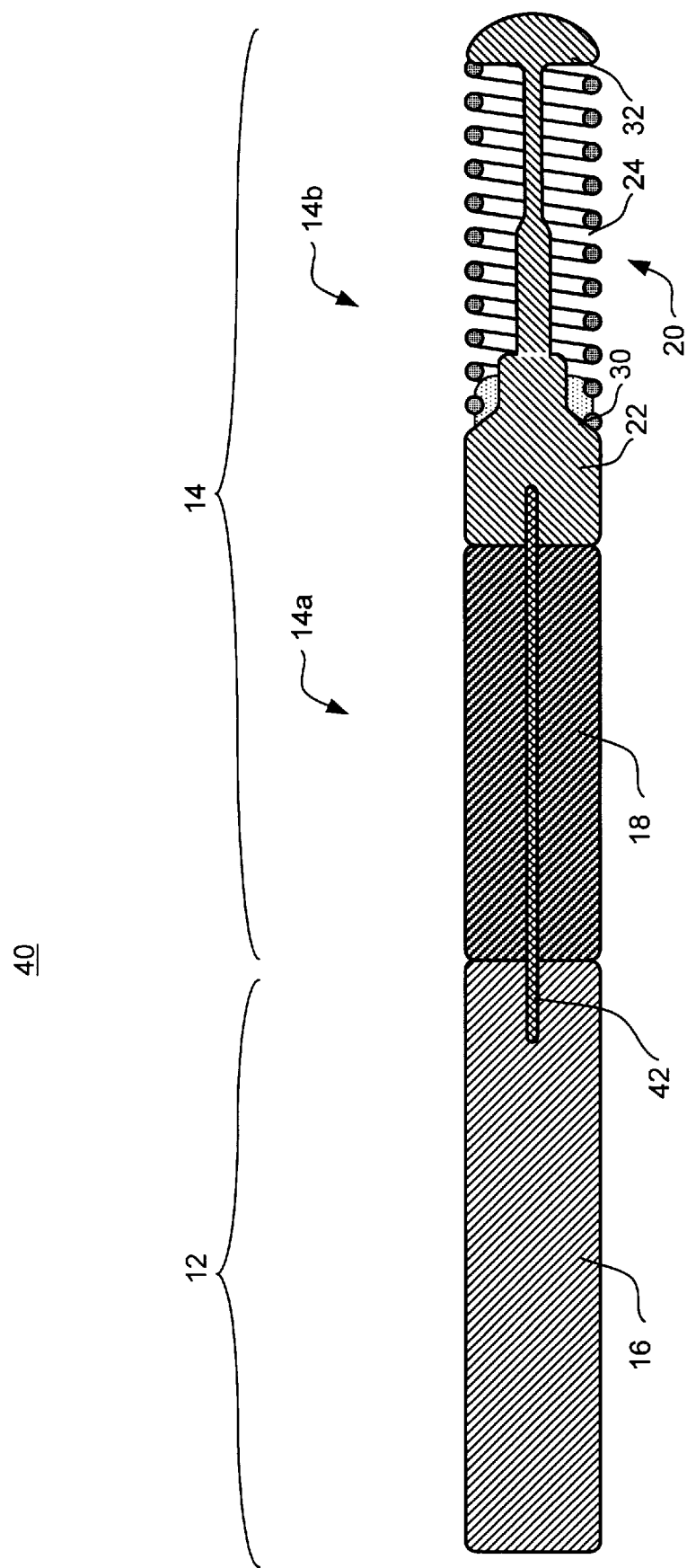
FIG. 2 is a longitudinal cross-sectional view of a second embodiment of a low attenuation guide wire of the present invention.
Figure 3:
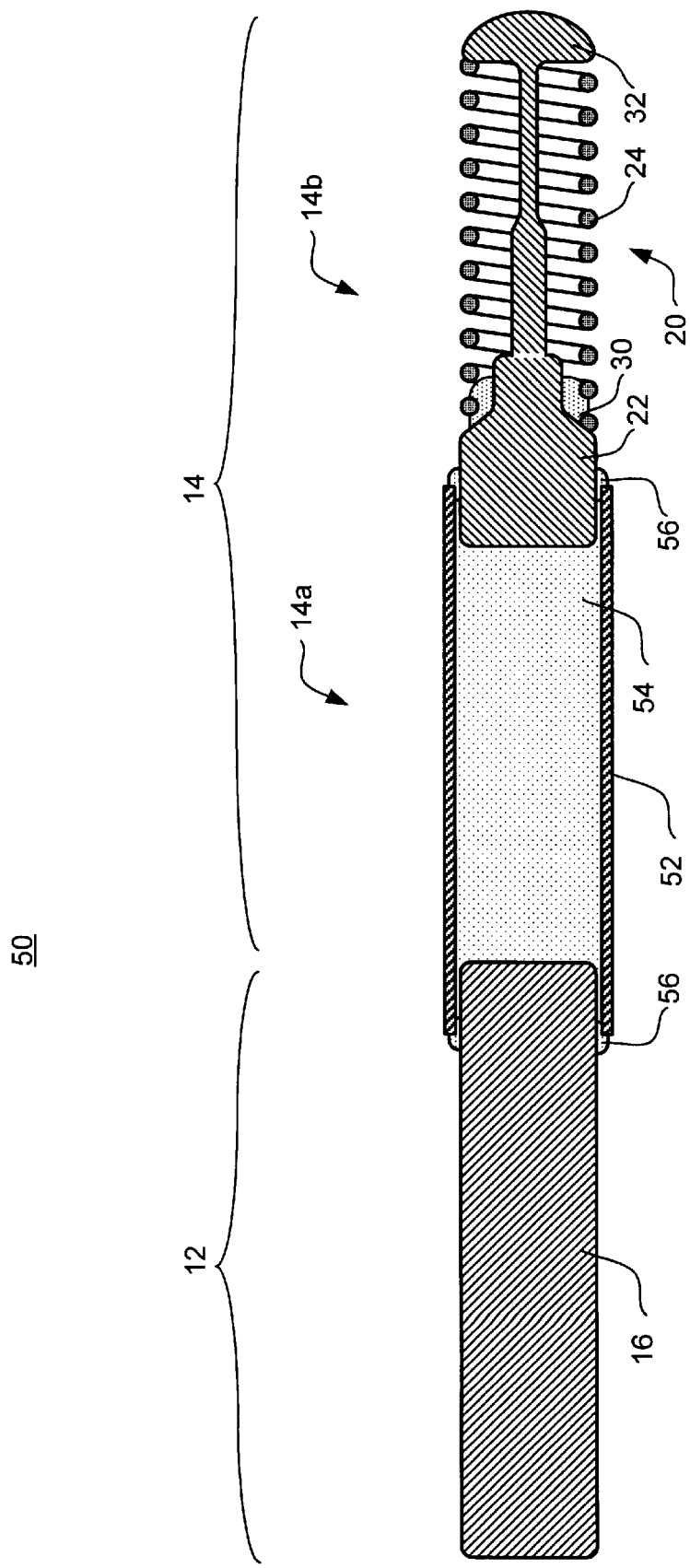
FIG. 3 is a longitudinal cross-sectional view of a third embodiment of a low attenuation guide wire of the present invention

Refer now to FIGS. 2 and 3 which illustrate longitudinal cross-sectional views of alternative embodiments of low attenuation guide wire in accordance with the present invention. All aspects of guide wires 40 and 50 are the same in form and function as guide wire 10 except as specifically described herein. The embodiments shown in FIGS. 1–3 are intended to demonstrate alternative means by which the various components comprising the proximal region 12 and the distal region 14 may be interconnected. Those skilled in the art will recognize that other arrangements of components and other means for connecting the various components may be utilized without departing from the scope or spirit of the present invention.

With specific reference to FIG. 2, guide wire 40 includes a proximal region 12 and a distal region 14. The distal region 14 includes a proximal end portion 14a and a distal end portion 14b. The proximal end portion 12 includes a core member 16. The proximal end portion 14a of the distal region 14 includes a core member 18. The distal end portion 14b of the distal region 14 includes a spring tip 20 having a core member 22 and a spring member 24.

Rather than using a polymeric sleeve 26 as described with reference to guide wire 10 illustrated in FIG. 1, guide wire 40 utilizes a mandrel 42 as a backbone that increases the integrity of the connections between the core members 16, 18 and 22. Core member 18 may be formed with a central bore to allow the mandrel 42 to pass therethrough. The distal end of core member 16 and the proximal end of core member 22 may include a bore extending partially therein to accommodate the proximal and distal ends of the mandrel 42. Mandrel 42 may be formed of a material selected from Group A of Table 1, so as to maintain low attenuation of the proximal end portion.

With this arrangement, the guide wire 40 may be assembled by rigidly connecting the proximal end of mandrel 42 inside the bore of the distal end of core member 16. Core member 18 may then be slid over mandrel 42 until the proximal end of core member 18 is disposed adjacent the distal end of core member 16. The core member 22 may then be rigidly connected to the protruding distal end of mandrel 42. Connection of the mandrel 42 to the core members 16 and 22 may be accomplished using conventional methods such as adhesive bonds, solder joints, crimping, swaging and the like. When assembled, the mandrel 42 serves as a backbone to interconnect or increase the integrity of the connections between the core members 16, 18, and 22.

With specific reference now to FIG. 3, guide wire 50 includes a proximal region 12 and a distal region 14 including a proximal end portion 14a and a distal end portion 14b. Guide wire 50 differs from guide wire 10 in that the proximal end portion 14a includes a tube 52 and a filler material 54, tube 52 may comprise a material selected from Group A of Table 1, tube 52 may be connected to the distal end of core member 16 and the proximal end of core member 22 utilizing a suitable connection means 56 such as an adhesive or a solder joint, depending on the compatibility of the materials. The proximal end portion 14a obtains its structural integrity from either tube 52 or filler material 54, depending on the material selected for tube 52. If tube 52 comprises a relatively stiff material such as a metal, the filler material 54 may comprise a polymer or other flexible material to reduce the tendency of the tube 52 to kink. Alternatively, if tube 52 comprises a relatively soft and pliable material such as a reinforced polymer, filler material 54 may comprises a relatively stiff material to add to the overall stiffness of the proximal end portion 14a.

In use, guide wires 10, 40 and 50 may be used in substantially the same fashion. When used in combination with a delivery device and radiation source wire as disclosed in European Patent Application No. 688 580 A1 to Verin et al. or as disclosed in U.S. Pat. No. 5,643,171 to Bradshaw et al., the guide wire 10/40/50 may be advanced prior to or simultaneously with the centering catheter. The guide wire 10/40/50 and the centering balloon catheter may be navigated through the vasculature using conventional fluoroscopic and radiographic techniques. Once the centering balloon is positioned adjacent the target site inside the vessel, the radiation source wire may be advanced into the treatment channel of the centering catheter until the radioactive distal end of the source wire is adjacent the target site. The proximal end portion 14a of the guide wire 10/40/50 is positioned adjacent the radioactive material disposed on the source wire such that the guide wire 10/40/50 does not significantly attenuate ionizing radiation emitted therefrom. Unlike the guide wires disclosed in Verin et al. and Bradshaw et al., the guide wire 10/40/50 of the present invention need not be retracted in a proximal direction in order to avoid blocking the radiation emitted by the source wire. Thus, the vessel wall is uniformly exposed to ionizing radiation.

From the foregoing, it is apparent that the guide wire 10/40/50 of the present invention is a significant improvement over conventional guide wires for use in intravascular ionizing radiation therapeutic procedures. The guide wire 10/40/50 includes a proximal region and a distal region, wherein the distal region is less attenuating to ionizing radiation than the proximal region. The distal region of the guide wire may remain disposed adjacent the distal ionizing radiation emitting portion of the source wire without significantly compromising the emission of radiation or the absorption of radiation by the vessel wall. Thus, the guide wire 10/40/50 does not need to be removed or retracted in order to effectively and uniformly deliver ionizing radiation to the vascular target site.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A guide wire for use in intravascular ionizing radiation therapy, comprising an elongate shaft having a proximal region and a distal region, the distal region being less attenuating to ionizing radiation than the proximal region.

2. A guide wire for use in intravascular ionizing radiation therapy, comprising an elongate shaft having a proximal region and a distal region, wherein the distal region includes a proximal end portion and a distal end portion, the proximal end portion being relatively less attenuating to ionizing radiation, and the distal end portion being relatively more radiopaque.

3. A guide wire as in claim 2, wherein the proximal end portion is less attenuating to low energy gamma ionizing radiation than the proximal region.

4. A guide wire as in claim 2, wherein the proximal end portion is less attenuating to high energy gamma ionizing radiation than the proximal region.

5. A guide wire as in claim 2, wherein the proximal end portion is less attenuating to beta ionizing radiation than the proximal region.

6. A guide wire as in claim 2, wherein the proximal end portion has a lower atomic number than the proximal region.

7. A guide wire as in claim 6, wherein the proximal end portion has an atomic number of less than 22.

8. A guide wire as in claim 6, wherein the proximal end portion has an atomic number of less than 15.

9. A guide wire as in claim 6, wherein the proximal end portion has an atomic number of less than 7.

10. A guide wire as in claim 2, wherein the proximal end portion has a lower atomic weight than the proximal region.

11. A guide wire as in claim 10, wherein the proximal end portion has an atomic weight of less than 47.

12. A guide wire as in claim 10, wherein the proximal end portion has an atomic weight of less than 29.

13. A guide wire as in claim 10, wherein the proximal end portion has an atomic weight of less than 13.

14. A guide wire as in claim 2, wherein the proximal end portion has a lower density than the proximal region.

15. A guide wire as in claim 14, wherein the proximal end portion has a density of less than 4.5 g/cm$^3$.

16. A guide wire as in claim 14, wherein the proximal end portion has a density of less than 2.3 g/cm$^3$.

17. A guide wire as in claim 14, wherein the proximal end portion has a density of less than 2.0 g/cm$^3$.

18. A guide wire as in claim 2, wherein the proximal end portion comprises graphite.

19. A guide wire as in claim 2, wherein the proximal end portion comprises aluminum.

20. A guide wire as in claim 2, wherein the proximal end portion comprises silicon.

21. A guide wire as in claim 2, wherein the proximal end portion comprises a polymer.

22. A guide wire as in claim 2, wherein the proximal end portion comprises a reinforced polymer.

23. A guide wire as in claim 2, wherein the proximal end portion comprises a polymer reinforced with a metallic coil.

24. A guide wire as in claim 2, wherein the proximal end portion comprises a polymer reinforced with a metallic braid.

25. A guide wire as in claim 2, wherein the proximal end portion comprises a polymer reinforced with glass fibers.

26. A guide wire as in claim 2, wherein the proximal end portion comprises a metal.

27. A guide wire as in claim 26, wherein the proximal end portion comprises a metal alloy.

28. A guide wire as in claim 2, wherein the proximal end portion comprises a single material.

29. A guide wire as in claim 2, wherein the proximal end portion comprises a plurality of materials.

30. A guide wire as in claim 2, wherein the proximal end portion comprises a composite of materials.

31. A system for administering intravascular ionizing radiation therapy, comprising:
    an intravascular device having a distal portion emitting ionizing radiation; and
    a guide wire comprising an elongate shaft having a proximal region and a distal region, the distal region being less attenuating to ionizing radiation than the proximal region, the distal region being disposed adjacent the distal portion of the intravascular device.

32. A system as in claim 31, wherein the distal region of the guide wire is less attenuating to low energy gamma ionizing radiation than the proximal region.

33. A system as in claim 31, wherein the distal region of the guide wire is less attenuating to high energy gamma ionizing radiation than the proximal region.

34. A system as in claim 31, wherein the distal region of the guide wire is less attenuating to beta ionizing radiation than the proximal region.

35. A system as in claim 31, wherein the distal region of the guide wire has a lower atomic number than the proximal region.

36. A system as in claim 31, wherein the distal region of the guide wire has a lower atomic weight than the proximal region.

37. A system as in claim 31, wherein the distal region of the guide wire has a lower density than the proximal region.

38. A system as in claim 31, wherein the distal region of the guide wire comprises a polymer.

39. A system as in claim 31, wherein the distal region of the guide wire comprises a metal.

40. A system as in claim 31, wherein the distal region of the guide wire comprises a single material.

41. A system as in claim 31, wherein the distal region of the guide wire comprises a plurality of materials.

42. A system as in claim 31, wherein the distal region of the guide wire comprises a composite of materials.

43. A guide wire for use in intravascular ionizing radiation therapy, comprising an elongate shaft having a proximal portion, a mid portion and a distal portion, the mid portion being less attenuating to ionizing radiation than the proximal and distal portions, and the distal portion being more radiopaque than the mid portion.

44. A method of administering intravascular ionizing radiation therapy to a treatment site in a patient's vascular system, the method comprising the steps of:

provjding an intravascular device having a distal portion emitting ionizing radiation;

providing a guide wire comprising an elongate shaft having a proximal region and a distal region, the distal region being less attenuating to ionizing radiation than the proximal region;

advancing the guide wire through the patient's vascular system until the distal region is disposed adjacent the treatment site; and advancing the intravascular device through the patient's vascular system until the distal portion emitting ionizing radiation is disposed adjacent the treatment site whereby radiation emitted from the distal portion of the intravascular device traverses the less attenuating distal region of the guide wire.

45. A method of administering intravascular ionizing radiation therapy as in claim 44, wherein the guide wire is disposed in a guide wire lumen contained at least partially in the intravascular device, and wherein the step of advancing the intravascular device comprises advancing the intravascular device over the guide wire until the distal portion emitting ionizing radiation is disposed adjacent the treatment site.

46. A method of administering intravascular ionizing radiation therapy as in claim 44, wherein the intravascular device includes a centering catheter and a source wire having a distal portion emitting ionizing radiation, and wherein the step of advancing the intravascular device comprises advancing the centering catheter device over the guide wire and advancing the source wire in the centering catheter until the distal portion emitting ionizing radiation is disposed adjacent the treatment site.

* * * * *